United States Patent [19]

Zampini

[11] Patent Number: Plant 7,279

[45] Date of Patent: Jul. 24, 1990

[54] SEEDLESS HYBRID MAPLE TREE NAMED CELZAM

[75] Inventor: James W. Zampini, Perry, Ohio

[73] Assignee: New Plants, Perry, Ohio

[21] Appl. No.: 290,842

[22] Filed: Dec. 27, 1988

Related U.S. Application Data

[63] Continuation of Ser. No. 129,401, Dec. 3, 1987, abandoned, which is a continuation of Ser. No. 895,801, Aug. 12, 1986, abandoned.

[51] Int. Cl.[5] ..... A01H 5/00

[52] U.S. Cl. ..... Plt./51

[58] Field of Search ..... Plt./51

*Primary Examiner*—Robert E. Bagwill

*Attorney, Agent, or Firm*—Watts, Hoffmann, Fisher & Heinke Co.

[57] ABSTRACT

The present invention relates to a new and distinct variety of hybrid maple, which was discovered by me as a variant in a block of Acer on my cultivated property at Perry, Ohio. More particularly, the present invention relates to a novel cultivar of an *Acer rubrum*×*Acer saccharinum* cross having unusual and distinctive characteristics, now available as Celzam.

3 Drawing Sheets

RELATED APPLICATIONS

This application is a continuation of Ser. No. 129,401, filed Dec. 3, 1987, now abandoned, which is a continuation of Ser. No. 895,801, filed Aug. 12, 1986, now abandoned.

TECHNICAL FIELD

The present invention relates to a new and distinct variety of seedless hybrid maple tree. This tree was discovered in 1967 in Zone 4 growing as a chance seedling among *Acer saccharinum* seedlings. Its two parents are *Acher saccharinum* and *Acer rubrum*. The discovery was made by Mr. James Zampini, and occurred at Indian Point Farm, Route 84, Perry, Ohio.

This selection is substantially seedless, rapid growth when young, and an extremely dense upright structure. This combination readily distinguishes it from either of its parents and other varieties of the genus.

DESCRIPTION OF THE DRAWINGS

The accompanying drawings (FIGS. 1 and 2) show typical specimens of the foliage and form of my new hybrid maple variety as depicted in color as nearly true as it is reasonably possible to make the same in a photographic illustration of this character. The color terminology is in reference to the Munsell Book of Color, hereinafter referred to as "Munsell".

Referring now more particularly to the drawings.

DESCRIPTION OF THE INVENTION

Strong upright growth and unusually dense branching attracted initial attention to this selection. The branches leave the straight central leader at an average angle of 45°. Branch tips curve upward and slightly inwards, creating a tightly ovoid crown. The dense structure is inherited from the *Acer rubrum* parent.

During the first five years a growth increment of 4 to 5 feet per year is considered average. Afterwards an average annual growth rate of 1 to 2 feet has been observed and calculated as typical for this tree. The tree is presently 40 feet tall, 18 feet wide, and has a caliper of 15 inches at grade. If grown on its own roots, it is expected to reach a height approximating 50 feet at maturity, and a width of 20 feet.

Common means of propagation involves taking softwood cuttings in early to mid June. This method provides a 98% rooting success rate. Budding onto *Acer saccharinum* understocks only achieves a 40% take.

The vegetative parts of this hybrid show some specific characteristics of each parent. The leaves are opposite, simple, and palmate, which is a trait shared by both *Acer rubrum* and *Acer saccharinum*. The foliar morphology is similar to *Acer rubrum* only in that it is occasionally 3-lobed and that it is a medium green (Munsell 2.5 BG 416) to dark green (Munsell 10 G 312) color. The remaining traits are generally characteristic of *Acer saccharinum*.

Leaf blade size averages from 3 to 6 inches in width and from 3½ to 4½ inches in length. Mature leaves are glabrous above with minute traces of white down below, particularly near the leaf axils. The pale green veins on the leaf underside appear yellow in contrast with the grey color. Newly emerging leaves are salmon in color with brown indumentum underneath, although this is not obvious at a distance and they quickly become green. Petiole lengths vary from 2 to 7 inches, are always glabrous, and are normally reddish on the side exposed to the sun. Leaf margins turn red in mid-September, with the whole leaf eventually maturing to a deep gold color in October. Leaf tips are acuminate, margins doubly serrate, sinuses entire, the bases hastate to sub-cordate. Most leaves are 5-lobed, occasionally 3-lobed, with the middle lobe normally 3-lobed.

Figure 1:
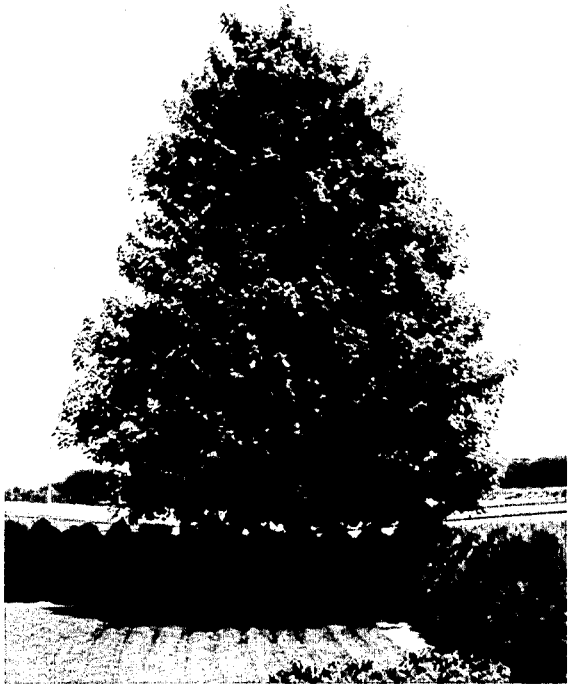
FIG. 1 shows a branchlet of such tree illustrating the foliage thereof.
Figure 2:
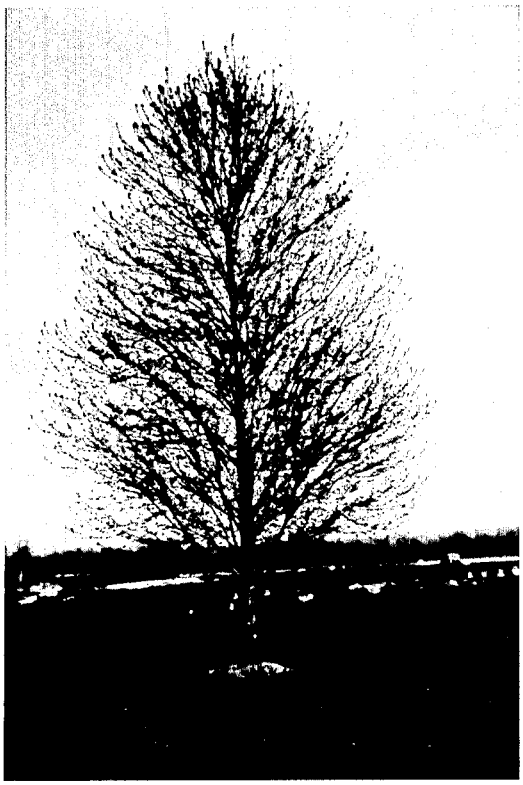
FIG. 2 shows the dormant tree illustrating the dense upright branching habit.
Figure 3:
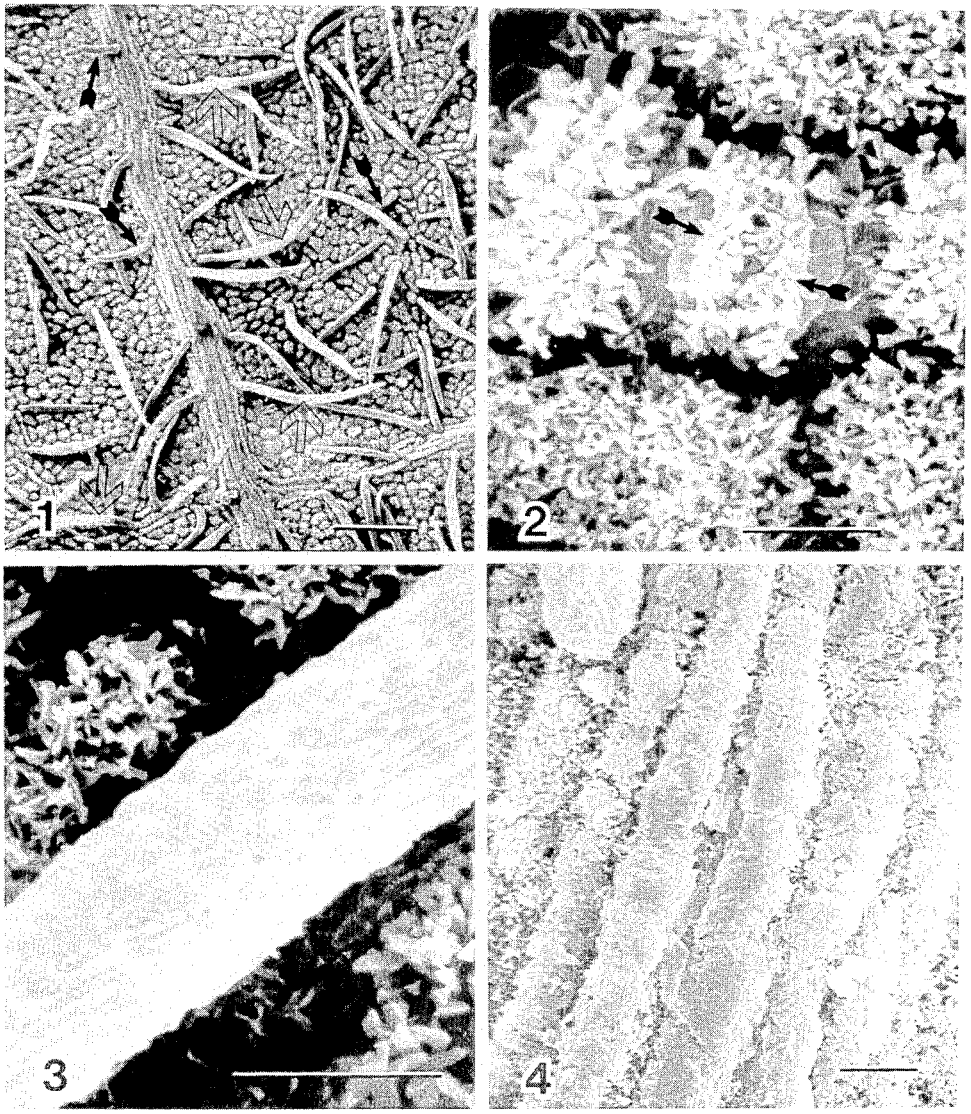
FIG. 3 shows a composite of electronmicrophotographs (Plates 1–4) illustrating hybrid traits of such tree in detail.
Figure 4:
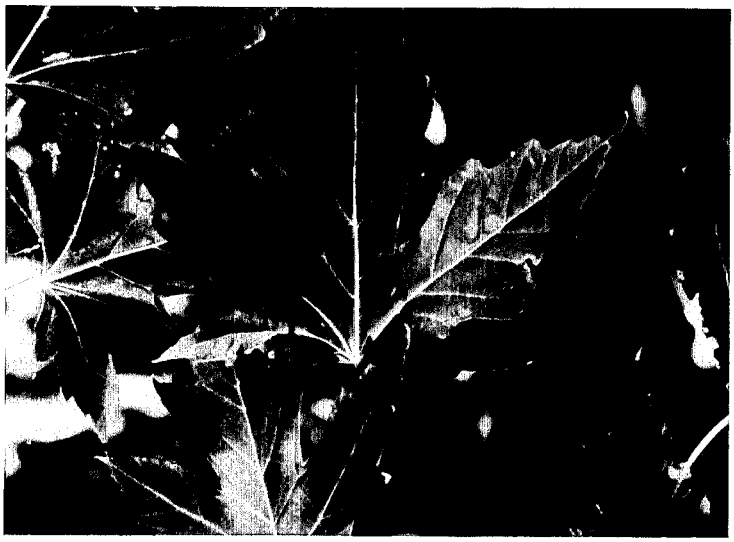
FIG. 4 shows the top surface of a tree leaf.
Figure 5:
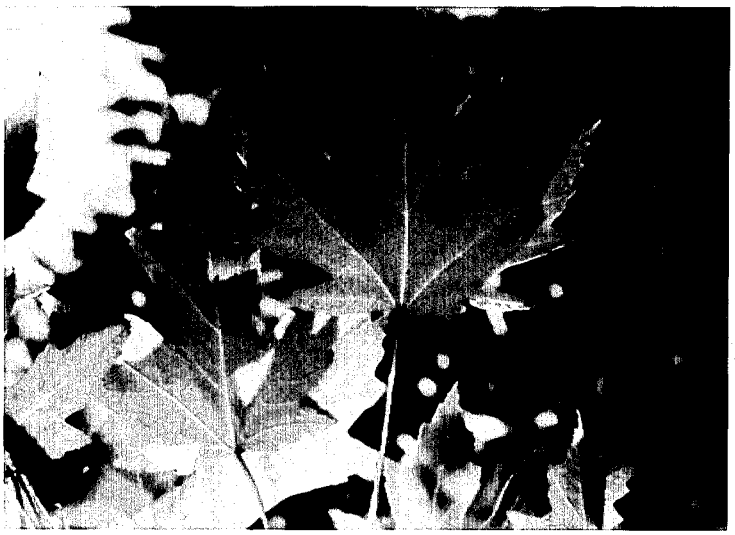
FIG. 5 shows the bottom surface of a tree leaf.

Abaxial Foliar Surfaces of the tree as described by Cultivar Identification With Scanning Electron Microscopy, a method developed by the Agricultural Research Service, U.S.D.A., at the Nursery Crops Research Laboratory, Delaware, Ohio. Unique features of tree in reference to plates 1–4 of FIG. 3 include:

Configuration of Foliar trichomes:

*Plate* 1 (*Magnification* × 150).—A. Designated with clear arrows. Slender and spiculate, as found on *Acer rubrum.* Bar = 50 μm. B. Designated with solid arrows. Obtuse and reduced, as found on *Acer saccharinum.* Bar = 50 μm.

Foliar stomata:

*Plate* 2 (*Magnification* × 3000).—Guard cell surfaces smooth with fringed stomatal lips (see arrows) as found on *Acer rubrum.* Bar = 50 μm.

Epicuticular wax:

*Plate* 2 (*Magnification* × 3000).—Wax granulate as found on *Acer rubrum. Acer saccharinum* is exfoliate. Bar = 5 μm.

Foliar trichome surface:

*Plate* 3 (*Magnification* × 3800).—Rugose, as found on *Acer saccharinum.* Bar = 5 μm.

Foliar vein surface:

*Plate* 4 (*Magnification* × 1500).—Coarse and rugose, as found on *Acer saccharinum.* Bar = 5 μm.

These electromicrophotographs were done with an Hitachi Model S-500 Scanning Electromicroscope. Plant specimens consisted of mature leaves collected on July 11, 1986.

Immature twigs are bright green and glabrous with slender vertical lenticels. A bright red band encircles the node nearly 1/16th inch wide in very new growth. Second year wood is medium brown with oval orange lenticels and is irregularly glaucous. Older stems are silver with small round, brown lenticels. Leaf scars darken to nearly black and extend in diameter, but never meet. The bark is smooth and grey. Stem pith is solid throughout, changing in color from white to cream to gold in mature twigs, with an increasingly rank odor. Vegetative buds are, in all respects, similar to *Acer saccharinum.*

The reproductive parts of this hybrid maple tree are perfect. The flower buds of this selection are identical with those of *Acer saccharinum,* varying only in that they open later. This is in accordance with *Acer rubrum.* Flowers appear in late March to early April before the leaves. They occur at the nodes of the previous year's wood or on the short spurs of older wood. Petals are a deep reddish color, opening to expose the numerous stamens of greenish-yellow. These stamens are perfect in form but produce no pollen. The pistils are also perfect in form, and are either red or greenish-yellow in color. There are numerous mature *Acer rubrum* and *Acer saccharinum* in the vicinity as potential pollinators. As the plant has never produced seed of any kind, I conclude that ovules are either not produced or are not viable as a result of an unknown hereditary factor. An irregularity during mitosis which rendered the plant with a chromosomal imbalance could account for this reproductive problem. Whatever the cause, the plant is substantially seedless, as are all successive generations thereof.

I claim:

1. A new and distinct variety of substantially seedless hybrid Acer, (maple tree), substantially as herein shown and described, characterized particularly be being substantially seedless, having rapid growth when young, and exhibiting an extremely dense upright structure.

* * * * *